(12) United States Patent
Glenn et al.

(10) Patent No.: US 10,270,386 B2
(45) Date of Patent: Apr. 23, 2019

(54) PHOTOVOLATIC POWERED CATHODIC PROTECTION PROBE

(71) Applicant: Oceaneering International, Inc., Houston, TX (US)

(72) Inventors: Casey Glenn, Houston, TX (US); Robert Groves, Crescent City, FL (US)

(73) Assignee: Oceaneering International, Inc., Houston, TX (US)

(*) Notice: Subject to any disclaimer, the term of this patent is extended or adjusted under 35 U.S.C. 154(b) by 17 days.

(21) Appl. No.: 15/253,258

(22) Filed: Aug. 31, 2016

(65) Prior Publication Data

US 2017/0057605 A1 Mar. 2, 2017

Related U.S. Application Data

(60) Provisional application No. 62/211,997, filed on Aug. 31, 2015.

(51) Int. Cl.
| | |
|---|---|
| *B63G 8/00* | (2006.01) |
| *H02S 40/30* | (2014.01) |
| *G01R 15/14* | (2006.01) |
| *C23F 13/02* | (2006.01) |
| *C23F 13/22* | (2006.01) |

(Continued)

(52) U.S. Cl.
CPC .............. *H02S 40/30* (2014.12); *C23F 13/02* (2013.01); *C23F 13/22* (2013.01); *B63B 59/00* (2013.01); *B63G 2008/005* (2013.01); *C23F 2213/31* (2013.01); *G01N 17/04* (2013.01)

(58) Field of Classification Search
CPC .......... H02S 40/30; C23F 13/02–13/22; G01N 17/04
See application file for complete search history.

(56) References Cited

U.S. PATENT DOCUMENTS 5,366,604 A * 11/1994 Stilley ..................... C23F 13/06
136/291
6,965,320 B1 * 11/2005 Casey ..................... F16L 55/48
324/71.2

(Continued)

FOREIGN PATENT DOCUMENTS

GB          2124382 A *  2/1984  .............. C23F 13/04

OTHER PUBLICATIONS

Britton et al., Recent Advances in Offshore Cathodic Protection Monitoring, Materials performance, No. 6, vol. 39, 2000, Jun. 2000.*

(Continued)

*Primary Examiner* — Huy Q Phan
*Assistant Examiner* — David B Frederiksen
(74) *Attorney, Agent, or Firm* — Maze IP Law, P.C.

(57) ABSTRACT

A remotely operated vehicle (ROV) compatible photovoltaic powered cathodic protection (CP) probe can measure voltage potential of subsea structures. In an embodiment, the CP's meter is integrated and able to send CP data topside. The CP meter's compact display module also houses the telemetry board to send CP readings, via an ROV serial, topside. The CP probe does not require a battery and can be used standalone or connected through an ROV to topside logging and display. Further, the CP probe can monitor a plurality of CP voltages and other conditions such as an electrical field gradient.

20 Claims, 2 Drawing Sheets

(51) Int. Cl.
*G01N 17/04* (2006.01)
*B63B 59/00* (2006.01)

(56) References Cited

U.S. PATENT DOCUMENTS

| | | | | |
|---|---|---|---|---|
| 7,425,249 B1 * | 9/2008 | Britton | ............... | C23F 13/02 |
| | | | | 204/196.02 |
| 2010/0039127 A1 * | 2/2010 | Orazem | ............... | C23F 13/04 |
| | | | | 324/718 |
| 2010/0270169 A1 * | 10/2010 | Howard | ............... | C23F 13/04 |
| | | | | 205/727 |
| 2012/0152559 A1 * | 6/2012 | Knox | ............... | C23F 13/04 |
| | | | | 166/345 |
| 2012/0205256 A1 * | 8/2012 | Catte | ............... | C23F 13/04 |
| | | | | 205/724 |
| 2018/0290717 A1 * | 10/2018 | Byrd | ............... | B63C 11/52 |

OTHER PUBLICATIONS

Polatrak® Deep C Meter 3000 AD™ ROV-mounted CP probe Operation manual, 2013, Document 358-MN03-ENG Rev A.*

* cited by examiner ained in the disclosed patent.

PHOTOVOLATIC POWERED CATHODIC PROTECTION PROBE

RELATION TO OTHER APPLICATIONS

This application claims priority through U.S. Provisional Application 62/211,997, filed Aug. 31, 2015.

BACKGROUND

The remotely operated vehicle (ROV) compatible photovoltaic powered cathodic protection (CP) probe can measure the voltage potential of subsea structures. In an embodiment, the CP's meter is highly integrated and able to send CP data topside, as opposed to using separate bulky telemetry bottle to interface with the ROV. The CP meter's compact display module also houses the telemetry board to send CP readings, via an ROV serial, topside. In embodiments, the CP probe would use ultrahard heat treated 440C stainless, or if necessary, a ground tungsten tip.

DRAWINGS

Various figures are included herein which illustrate aspects of embodiments of the disclosed inventions.

DESCRIPTION OF EXEMPLARY EMBODIMENTS

Figure 1:
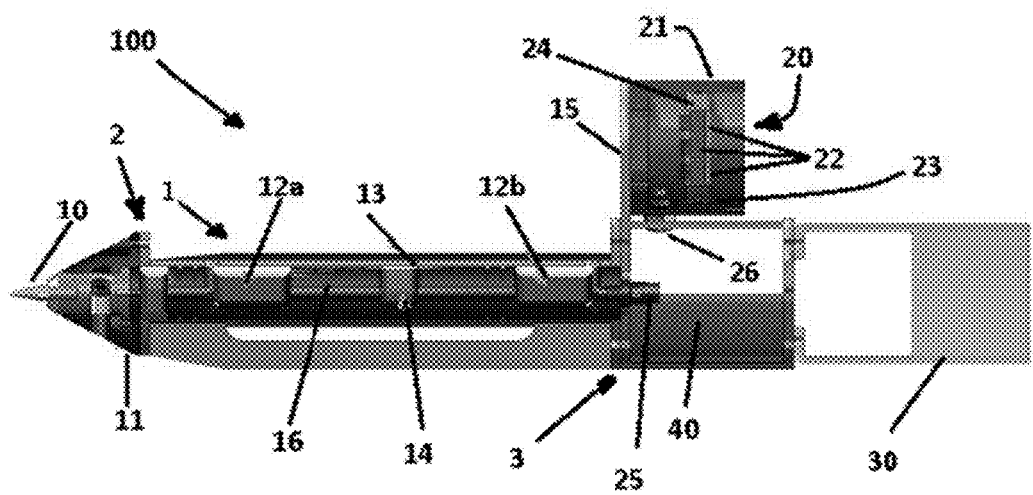
FIG. 1 is a cutaway view in partial perspective of an exemplary CP probe.

Referring now to FIG. 1, ROV compatible cathodic protection CP probe 100 comprises housing 1; isolation cap 11 disposed about first end 2 of housing 1; probe tip 10, disposed proximate first end 2 of housing 1, first portion 10a of probe tip 10 operatively exposed to an exterior portion of housing 1 proximate isolation cap 11; one or more reference cells 12 (generally referred to herein as "12" with exemplary reference cells referred to herein as "12a" and/or "12b") disposed within housing 1 and operatively in communication with probe tip 10; electrical source 20 operatively in communication with reference cell 12; and ROV handle 30 disposed about second end 3 of housing 1 opposite the first end 2 of housing 1. Protective extension 40 may be disposed intermediate housing 1 and ROV handle 30.

Housing 1 may be of any appropriate shape but is typically tubular and typically constructed of a material suitable for subsea deployment. Isolation cap 11 may also be of any suitable material such as polytetrafluoroethylene (PTFE).

Reference cell 12 may comprise silver and/or silver chloride and may be disposed within a cell extension holder within housing 1, where the cell extension holder comprises any suitable material such as PTFE.

As will be apparent to those of ordinary skill in electrical arts, reference cell 12 may comprise a plurality of reference cells, e.g. 12a, 12b, disposed within housing 1 and operatively in communication with probe tip 10 such as being placed in parallel or series as the need requires.

Probe tip 10 comprises at least one of a heat treated 440C stainless tip or a ground tungsten tip. In certain embodiments, probe tip 10 comprises an ultrahard tip comprising a material suitable for subsea deployment which is also suitable for use as a cathodic probe.

Figure 2:
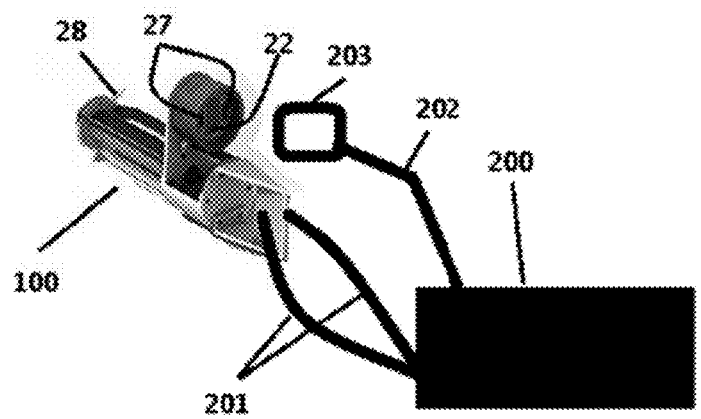
FIG. 2 is a view in partial perspective of an exemplary CP probe and ROV.
Figure 3:
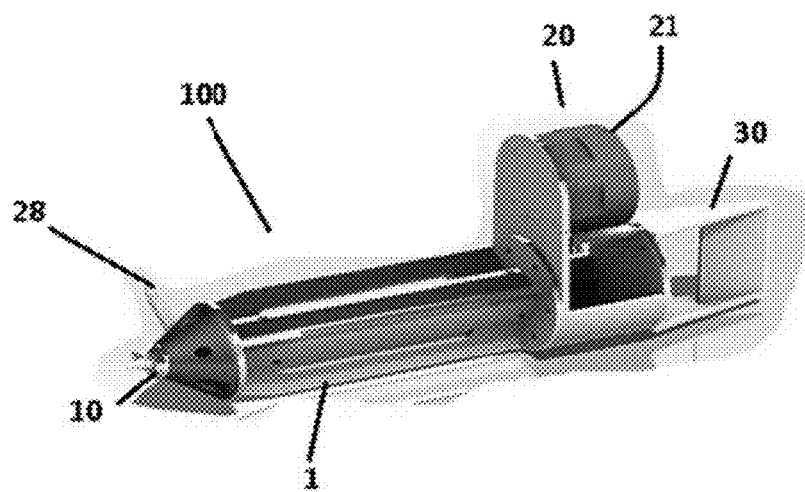
FIG. 3 is a side view in partial perspective of an exemplary CP probe.

In embodiments, electrical source 20 comprises power housing 21 typically constructed of a material suitable for subsea deployment; one or more photovoltaic cells 22 (FIG. 2) disposed proximate power housing 21 and operatively in communication with reference cell 12, each photovoltaic cell 27 adapted to be powered by light 203 from remotely operated vehicle (ROV) 200; ROV serial interface 23 operatively in communication with reference cell 12 and photovoltaic cell 27; and telemetry electronics 24 operatively in communication with ROV serial interface 23 and reference cell 12.

Telemetry electronics 24 are typically configured to send data representative of CP readings such as back to ROV 200 or a surface location.

In embodiments, electrical source 20 further comprises standalone display 22 operatively in communication with photovoltaic cell 27 (FIG. 2) and telemetry electronics 24. Standalone display 22 may detached from power housing 21 and mounted on an ROV porch. In embodiments, standalone display 22 comprises a set of three voltage meter displays which typically display CP voltage, backup CP voltage, and a water voltage gradient which may be obtained such as from one or more sensors 28 (FIG. 2) which operatively in communication with telemetry electronics 24. Although illustrated as being disposed proximate first end 2 of housing 1, sensors 28 may be disposed at any appropriate place along housing 1.

In addition, electrical source 20 may further comprise one or more interfaces 25 to an external power source. As such, interface 25 may be operatively in communication with reference cell 12 and comprise a detachable electrical source interface. In embodiments, electrical source interface 25 may further comprise a built in connection to a microtooling control unit (μTCU) 26, disposed inside power housing 21, where μTCU 26 is configured to allow isolated communication and power to pass out of standalone meter 22 to a topside tooling computer for live display and logging of the CP voltage readings.

In the operational of an exemplary embodiment, referring still to FIG. 1, CP probe 100 can be used to measure voltage potential of subsea structures. CP probe 100 may allow for a plurality of data acquisition modes in one housing, i.e. CP probe 100 may be used in either a standalone mode or connected through ROV 200 to a topside display and/or logger.

A need for battery power for a CP probe may be lessened or eliminated by providing power to CP probe 100, as described above, by directing light from ROV light source 203 onto photovoltaic cell 12. Typically, CP probe 100 is operatively placed such that standalone display 22 is in communication with photovoltaic cell 12 and CP probe 100 powered using ROV light source 203.

Once powered and placed into position such as via ROV 200 (FIG. 2), a predetermined set of readings may be displayed on standalone display 22. Each of the predetermined set of readings is typically displayed on a unique meter display of standalone display 22, i.e. standalone display 22 may comprise a plurality of meter displays. Where standalone display 22 comprises three voltage meter displays, the predetermined set of readings on the three voltage meter displays may comprise a CP voltage reading, a backup CP voltage reading, and a water voltage gradient reading, typically one such reading per voltage meter display.

CP probe 100 may be selectively attached to and/or detached from ROV manipulator 201 (FIG. 2) during subsea operations in favor of other tools.

In embodiments, CP probe 100 may be integrated with an ROV telemetry system. In these embodiments, a predetermined voltage reading obtained by CP probe 100 may be provided to an ROV serial interface such as via ROV serial interface 23 which is made accessible from an externally accessible serial communications port.

If present, µTCU 26 may be provided inside power housing 21 and placed into communication with standalone display 22. µTCU 26 may then be used to isolate communications and power and the isolated communications and power allowed to pass out of CP probe 100 to a topside tooling computer for live display and logging of the CP voltage readings.

One or more hydraulic hoses, e.g. ROV hoses, may be used to carry signal wires from the CP probe back to an ROV.

The foregoing disclosure and description of the inventions are illustrative and explanatory. Various changes in the size, shape, and materials, as well as in the details of the illustrative construction and/or an illustrative method may be made without departing from the spirit of the invention.

The invention claimed is:

1. A remotely operated vehicle ("ROV") compatible cathodic protection (CP) probe, comprising:
   a. a housing;
   b. an isolation cap disposed about a first end of the housing;
   c. a probe tip disposed proximate the first end of the housing, a first portion of the probe tip operatively exposed to an exterior portion of the housing proximate the isolation cap;
   d. a reference cell disposed within the housing and operatively in communication with the probe tip;
   e. an electrical source operatively in communication with the reference cell, the electrical source comprising:
      i. a power housing;
      ii. a photovoltaic cell disposed proximate the power housing and operatively in communication with the reference cell, the photovoltaic cell adapted to be powered by ambient light;
      iii. an ROV serial interface operatively in communication with the reference cell and the photovoltaic cell; and
      iv. telemetry electronics operatively in communication with the ROV serial interface and the reference cell, the telemetry board configured to send CP readings; and
   f. an ROV handle disposed about a second end of the housing opposite the first end of the housing.

2. The ROV compatible cathodic protection (CP) probe of claim 1, wherein the probe tip comprises at least one of a heat treated 440C stainless tip or a ground tungsten tip.

3. The ROV compatible cathodic protection (CP) probe of claim 1, wherein the probe tip comprises an ultrahard tip.

4. The ROV compatible cathodic protection (CP) probe of claim 1, wherein the electrical source further comprises a standalone three voltage meter display operatively in communication with the photovoltaic cell and the telemetry electronics.

5. The ROV compatible cathodic protection (CP) probe of claim 4, wherein the standalone three voltage meter display comprises displays of CP voltage, backup CP voltage, and a water voltage gradient.

6. The ROV compatible cathodic protection (CP) probe of claim 1, wherein the electrical source further comprises an interface to an external power source, the interface operatively in communication with the reference cell.

7. The ROV compatible cathodic protection (CP) probe of claim 1, wherein the electrical source interface comprises a detachable electrical source interface.

8. The ROV compatible cathodic protection (CP) probe of claim 1, wherein the electrical source interface comprises a built in connection to a micro-tooling control unit (µTCU), disposed inside the same display housing, the µTCU configured to allow isolated communication and power to pass out of the meter to a topside tooling computer for live display and logging of the three CP voltage readings.

9. The ROV compatible cathodic protection (CP) probe of claim 1, wherein the reference cell comprises a plurality of reference cells disposed within the housing and operatively in communication with the probe tip.

10. The ROV compatible cathodic protection (CP) probe of claim 1, wherein the ambient light comprises light supplied from a remotely operated vehicle (ROV).

11. A method of providing a cathodic protection (CP) probe, the cathodic protection probe comprising a housing, an isolation cap disposed about the first end of the housing, a probe tip, disposed at a first end of the housing where a first portion of the probe tip operatively exposed to an exterior portion of the housing proximate the isolation cap, a reference cell disposed within the housing and operatively in communication with the probe tip, an electrical source operatively in communication with the reference cell where the electrical source interface comprises a power housing, a photovoltaic cell disposed proximate the power housing and operatively in communication with the reference cell, the photovoltaic cell adapted to be powered by a remotely operated vehicle ("ROV") light, an ROV serial interface operatively in communication with the reference cell and a telemetry board operatively in communication with the ROV serial interface and the reference cell, the telemetry board configured to send CP readings, the electrical source interface further comprising a standalone meter display operatively in communication with the photovoltaic cell, and an ROV handle disposed about a second end of the housing opposite the first end of the housing, the method comprising:
   a. the cathodic protection probe into contact with a subsea structure using an ROV via the ROV handle;
   b. operatively placing the standalone meter display into communication with the photovoltaic cell;
   c. eliminating a need for battery power by providing power to the probe by directing light from an ROV light source onto the photovoltaic cell; and
   d. displaying a predetermined set of readings on the standalone meter display, the reading obtained by the CP probe in contact with the subsea structure.

12. The method of providing a cathodic protection probe of claim 11, wherein the predetermined set of readings on the standalone voltage meter display comprises a CP voltage reading, a backup CP voltage reading, and a water voltage gradient reading.

13. The method of providing a cathodic protection probe of claim 11, wherein:
   a. the standalone meter display comprises a standalone three voltage meter display; and
   b. the predetermined set of readings on the standalone three voltage meter display comprises a CP voltage reading, a backup CP voltage reading, and a water voltage gradient reading.

14. The method of providing a cathodic protection probe of claim 13, wherein each of the predetermined set of readings is displayed on a unique meter display of the standalone three voltage meter display.

15. The method of providing a cathodic protection probe of claim 11, further comprising selectively attaching and detaching the cathodic protection probe to an ROV manipulator during subsea operations in favor of other tools.

16. The method of providing a cathodic protection probe of claim 11, further comprising:
   a. integrating the CP probe with an ROV telemetry system;
   b. providing a predetermined voltage reading obtained by the CP probe to an ROV serial interface; and
   c. making the ROV serial interface accessible from an externally accessible serial communications port.

17. The method of providing a cathodic protection probe of claim 16, further comprising:
   a. providing a micro tooling control unit (µTCU) inside the display housing;
   b. placing the µTCU into communication with the meter;
   c. using the µTCU to isolate communications and power; and
   d. allowing the isolated communications and power to pass out of the meter to a topside tooling computer for live display and logging of the three CP voltage readings.

18. The method of providing a cathodic protection probe of claim 11, further comprising detaching the standalone voltage meter display from the meter body (21) and mounting it on an ROV porch.

19. The method of providing a cathodic protection probe of claim 11, further comprising using a hydraulic hose to carry signal wires from the CP probe back to an ROV.

20. The ROV compatible cathodic protection (CP) probe of claim 11, further comprising using the CP probe in either a standalone mode or connected through an ROV to a topside display and/or logger.

* * * * *